United States Patent [19]

DesJardin et al.

[11] Patent Number: 5,157,173
[45] Date of Patent: Oct. 20, 1992

[54] PROCESS FOR 4-CHLOROBENZOTRICHLORIDE

[75] Inventors: Michael A. DesJardin, San Ramon; Clark P. Allphin, Concord, both of Calif.

[73] Assignee: DowElanco, Indianapolis, Ind.

[21] Appl. No.: 764,660

[22] Filed: Sep. 24, 1991

[51] Int. Cl.$^5$ ...................... C07C 17/22; C07C 17/14
[52] U.S. Cl. .................................... 570/196; 570/191; 570/197; 570/207; 570/208; 204/157.97
[58] Field of Search ............... 570/197, 191, 196, 207, 570/208; 204/157.97

[56] References Cited

U.S. PATENT DOCUMENTS 3,350,467 10/1967 Lasco et al. ..................... 570/188
3,683,029 8/1972 Dorrentos ........................ 570/207
3,836,445 9/1974 Sano et al. .
3,928,478 12/1975 Johnson .
3,952,065 4/1976 Mrva et al. .

FOREIGN PATENT DOCUMENTS 0424654 2/1942 Japan ................................. 570/197

OTHER PUBLICATIONS

Organic Chemistry, 4th Ed.; R. T. Morrison & R. N. Boyd; 1983, pp. 640-643.
Activated Carbon; J. W. Hassler; 1974, pp. 248-273 & 341-354.
Chlorine; J. S. Sconce, Editor-in-Chief; 1962, pp. 21-45 by E. J. Laubusch pp. 834-863 by P. E. Hoch.
Kirk-Othmer Encyclopedia of Chemical Technology, Third Ed., vol. 5, pp. 819-822, 825, 828, 831-832, and 834-836.
Jinichiro et al., "Chlorination of Aromatic Compound at Side Chains", *Chemical Abstracts*, vol. 89,89:215045s, 1978, p. 560.

*Primary Examiner*—Marianne M. Cintins
*Assistant Examiner*—Michael B. Hydorn
*Attorney, Agent, or Firm*—D. Wendell Osborne

[57] ABSTRACT 4-chlorobenzotrichloride was prepared by the chlorination of p-xylene in the vapor phase at a temperature above about 200° C. in the presence of an activated carbon catalyst and water. An approximately 75 percent calculated yield was obtained at 250° C. using a wide-pore activated carbon catalyst.

10 Claims, No Drawings

PROCESS FOR 4-CHLOROBENZOTRICHLORIDE

BACKGROUND OF THE INVENTION

The present invention relates to a process for the production of 4-chlorobenzotrichloride (1-chloro-4-(trichloromethyl)benzene).

4-Chlorobenzotrichloride is a valuable intermediate used in the commercial production of herbicides. It is generally prepared from toluene by ring chlorination to 4-chlorotoluene and followed by methyl group chlorination to the desired compound (*Kirk-Othmer Encyclopedia of Chemical Technology*, Third Ed., Vol. 5, pages 819-836). This method has critical disadvantages, including the disadvantage that undesirable isomers are formed as by-products in the initial ring chlorination. Other methods of preparing 4-chlorobenzotrichloride include a process wherein toluene is first converted to p-toluenesulfonyl chloride with chlorosulfonic acid and this is further chlorinated (U.S. Pat. No. 3,952,065). This method is relatively complex, requires a relatively expensive reagent and also produces undesirable by-product isomers (in the sulfonation step). New, isomer-specific methods of producing 4-chlorobenzotrichloride in an economical manner would be of considerable value.

SUMMARY

It has now been found that 4-chlorobenzotrichloride can be prepared in a simple, isomer-specific process by chlorinating p-xylene (1,4-dimethylbenzene) in the vapor phase in the presence of a carbon catalyst.

The invention includes a process for preparing 4-chlorobenzotrichloride which comprises chlorinating p-xylene in the vapor phase in the presence of water and an activated carbon catalyst at a temperature above about 200° C.

Water to p-xylene molar ratios of at least about 1 and temperatures of between about 200° C. and about 300° C. are preferred. Wide-pore activated carbon catalysts are generally preferred.

DETAILED DESCRIPTION OF THE INVENTION

The chemical reactions taking place in the process of the present invention are given by the following equation:

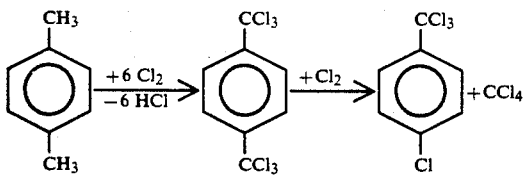

The p-xylene first reacts with chlorine in a chlorination reaction to produce 1,4-bis(trichloromethyl)benzene and this reacts further with chlorine by chlorinolysis to produce the desired 4-chlorobenzotrichloride and carbon tetrachloride.

The methyl group chlorination (first) reaction step of the process takes place more readily than does the chlorinolysis (subsequent) reaction step. It generally takes place well without the necessity of using an activated carbon catalyst and without the addition of water. The chlorination reaction step, further, takes place at temperatures as low as about 100° C. It is clearly possible, and is sometimes preferable, to carry out the present process using two different reactors with different reaction conditions for the two steps. The effluent of the first reactor is preferably fed to the subsequent reactor without condensation. It is further possible, and is often preferable to carry out the process in a single reactor with two distinct reaction zones having different reaction conditions, a first zone for the methyl group chlorination reaction and a subsequent zone for the chlorinolysis reaction. The reaction conditions described herein, unless otherwise noted, are those conducive to the chlorinolysis reaction. Reaction conditions that are specifically conducive to the methyl group chlorination reaction are known in the art. Thus, the intermediate 1,4-bis(trichloromethyl)benzene can be prepared by the chlorination of p-xylene in the vapor phase at about 140° C. to about 250° C., optionally in the presence of free radical catalysts such as ultraviolet light.

The process of the present invention is carried out in a vapor phase reactor system, generally in a continuous vapor phase reactor system. The design of the system is not critical, but it should provide means for good mixing of the reactants and water and provide means for good contact between the reactants and the catalyst. An upright packed column which is equipped with an inlet tube having concentric pipes for the p-xylene, water, and chlorine, for example, can be employed. It is also possible, and in some instances preferable to mix vapors of p-xylene, chlorine, and water in a separate vessel and feed the mixture to the reactor. Other reactors, such as horizontally oriented column reactors packed with activated carbon can also be employed. It is possible, and in many situations preferable to divide the reactor into a first noncatalytic section and a second catalytic section. The components of the reactor system should be compatible with chlorine and hydrogen chloride in an environment that includes water. Nickel or a nickel alloy, such Hastalloy ™ C, quartz, and glass are generally suitable.

The p-xylene, chlorine, and water can each be used in the process without further dilution or any one or all can be diluted with an inert gas, such as argon or nitrogen, or with an inert solvent, such as carbon tetrachloride or tetrachloroethylene before being fed to the reactor. The inert gas or solvent can also be fed to the reactor as a separate stream. Excess water (steam) can be used as a diluent.

The present process takes place at temperatures above about 200° C. It is preferred to operate at temperatures below about 300° C. because undesirable by-products are formed at higher temperatures. The process is generally conducted at a pressure wherein the reactants and products are volatile at the chlorination temperature, but readily condensed by cooling. It is convenient to carry out the process at ambient pressures; that is, atmospheric pressure plus any back-pressure in the reactor system.

Activated carbon is required as a catalyst in the present invention. Activated carbons from different sources are not identical in catalytic activity, but all activated carbons have at least some utility in the process. Activated carbon can be defined as an amorphous form of carbon characterized by having a high adsorptivity for many gases, vapors, and colloidal solids and having a very large internal surface area. It can be made by pyrolyzing hydrocarbons, wood, nut shells, animal bones and other carbonaceous materials and can be activated by heating at about 600° C. to about 1000° C. with steam or carbon dioxide. Wide-pore activated carbons, which have average pore diameters of at least 80 Angstroms and are prepared by pyrolyzing certain synthetic polymeric materials as described in U.S. Pat. No. 3,978,000, are sometimes preferred. It is generally preferred to employ the activated carbon in a granulated or pelletized form rather than in powder form.

The amount of activated carbon employed depends upon not only the catalytic activity of the particular activated carbon, but also upon the geometry of the reactor employed, the flow rate of the reactants in the reactor, and the temperature and pressure within the reactor. The contact time of the reactants with the catalyst is, perhaps, the most important measure. Contact times of at least 0.1 second are generally preferred. Contact times of less than about 30 seconds are typical. An amount of activated carbon sufficient to ensure a significant conversion of the p-xylene used to 4-chlorobenzotrichloride is employed. Activated carbon catalysts that have lost activity can be reactivated by heating with steam as is known in the art.

The molar ratio of chlorine to p-xylene in the process is theoretically 7 to 1 and it is preferred to carry out the process in a molar ratio of at least 7 to 1, although some product is obtained at all ratios greater than about 6 to 1. It is more preferred to employ an excess of chlorine; that is, a molar ratio of greater than 7 to 1 to about 30 to 1.

Water is required as a component of the reaction mixture to achieve good yields of 4-chlorobenzotrichloride. The non-adsorbed water is, of course, in the form of steam within the chlorination reactor. Any amount of water is beneficial and amounts greater than an amount equimolar to the p-xylene employed is preferred. It is often more preferred to use about 1 to about 10 moles of water per mole of p-xylene. On the other hand, it is sometimes more preferred to use larger amounts of water and have it perform as a diluent (steam) as well as a required component.

The 4-chlorobenzotrichloride prepared by the process of the present invention is generally recovered by condensing the effluent gas stream from the reactor. It can be purified by distillation as is known in the art.

The following examples are presented to illustrate the invention and should not be construed as limiting.

EXAMPLES

Example 1—Chlorination of p-Xylene at 250° C.

A 0.40 cm inside diameter Pyrex TM U-tube reactor was housed in a convection oven so that the ends were exposed and there was a 42 cm section that was heated. The inlet leg of the U-tube reactor was connected to both a chlorine cylinder and a helium cylinder, the latter separated from the inlet leg by two additional U-tubes, the one closest to the reactor containing p-xylene and the other containing water in the bottom section in amounts that left some head space. The outlet leg of the U-tube reactor was connected to an in-line gas chromatograph sampling tube and then to a condenser and a scrubber. The gas chromatograph was equipped with both flame ionization and mass selective detectors. American Cyanamid wide-pore carbon catalyst, lot No. SN-5701, was crushed and, after removing the dust, was packed into the last 9.0 cm of the heated section of the exit leg of the U-tube reactor. The total volume of the heated section of the tube was measured to be 5.1 cm$^3$ and the volume of catalyst was 1.1 cm$^3$. The catalyst was conditioned by heating the U-tube reactor to 390° C. and allowing helium saturated with water at 25° C. (approximately 3 mole percent) to pass through for a short period. The temperature of the U-tube reactor was then adjusted to 249° C. Helium was passed through the water and the p-xylene containing U-tubes at the rate of 13.6 cm$^3$/min (at standard temperature and pressure) and into the reactor. Chlorine was passed into the reactor at the rate of 4.9 cm$^3$/min. This resulted in a total input stream flowing at 18.5 cm$^3$/min and containing about 0.8 mole percent p-xylene, about 2.3 mole percent water, and about 26 mole percent chlorine. The contact time with the activated carbon was calculated to be approximately 0.7 sec. The effluent stream was analyzed periodically. When the system had stabilized the effluent contained the following organic materials (normalized area percent) 1,4-bis(trichloromethyl)benzene, 65.7; 4-chlorobenzotrichloride, 25.7: 1,4-dichlorobenzene, 1.4: 3,4-dichlorobenzotrichloride, 1.9: 2-chloro-1,4-bis(trichloromethyl)benzene, 1.2: unknowns, 4.6; and carbon tetrachloride. The conversion of p-xylene to 1,4-bis(trichloromethyl)benzene was, accordingly, essentially quantitative and the conversion of 1,4-bis(trichloromethyl)benzene to 4-chlorobenzotrichloride was about 75 percent efficient. The calculated yield, including recycle of the intermediate, was, accordingly, 75 percent.

Example 2—Chlorination of p-Xylene at About 325° C.

Example 1 was repeated except that the temperature was maintained at 326° C. Helium was passed through the water and the p-xylene containing U-tubes at the rate of 14.2 cm$^3$/min (at standard temperature and pressure) and into the reactor. Chlorine was passed into the reactor at the rate of 8.6 cm$^3$/min. This resulted in a total input stream flowing at 22.8 cm$^3$/min and containing 0.6 mole percent p-xylene, 1.8 mole percent water, and 38 mole percent chlorine. The contact time of the reactants with the catalyst was 0.48 sec. The pressure drop across the reactor was about 1.5 psi (10.4 kPa). When the system had stabilized the effluent contained the following organic materials (normalized area percent): 1,4-bis(trichloromethyl)benzene, 44.3: 4-chlorobenzotrichloride, 14.2; 1,4-dichlorobenzene, 1.0: tri-, tetra-, penta-, and hexachlorobenzenes, 5.4; 3,4-dichlorobenzotrichloride, 12.2; trichlorobenzotrichlorides, 3.8: 2-chloro-1,4-bis(trichloromethyl)benzene, 10.1: unknowns, 0.8: and carbon tetrachloride, 2.5. The conversion of p-xylene to 1,4-bis(trichloromethyl)benzene was, accordingly, essentially quantitative and the conversion of 1,4-bis(trichloromethyl)benzene to 4-chlorobenzotrichloride was about 30 percent efficient. The calculated yield, including recycle of the intermediate, was, accordingly, 30 percent.

What is claimed is:

1. A process for preparing 4-chlorobenzotrichloride which comprises chlorinating p-xylene in the vapor phase in the presence of water and an activated carbon catalyst at a temperature above about 200° C.

2. A process according to claim 1 wherein the temperature is between about 200° C. to about 300° C.

3. A process according to claim 1 wherein the molar ratio of water to p-xylene is at least 1.

4. A process according to claim 1 wherein the catalyst is a wide-pore activated carbon.

5. A process for preparing 4-chlorobenzotrichloride which comprises chlorinating p-xylene in the vapor phase in a first step at a temperature of about 140° C. to about 250° C., optionally in the presence of ultraviolet light, to obtain 1,4-bis(trichloromethyl)benzene as an intermediate and, in a subsequent step, at a temperature above about 200° C. in the presence of water and an activated carbon catalyst.

6. A process according to claim 5 wherein, in the subsequent step, the temperature is between about 200° C. to about 300° C.

7. A process according to claim 5 wherein, in the subsequent step, the molar ratio of water to p-xylene is at least 1.

8. A process according to claim 5 wherein, in the subsequent step, the catalyst is a wide-pore activated carbon.

9. A process according to claim 5 wherein the first and the subsequent steps are carried out in separate reactors.

10. A process according to claim 5 wherein the first and the subsequent steps are carried out in a single reactor having two distinct reaction zones.

* * * * *